United States Patent [19]

Campbell et al.

[11] 4,430,333

[45] Feb. 7, 1984

[54] DIHYDROPYRIDINE ANTI-ISCHAEMIC AND ANTIHYPERTENSIVE AGENTS

[75] Inventors: Simon F. Campbell, Deal; Peter E. Cross, Canterbury; John K. Stubbs, Deal, all of England

[73] Assignee: Pfizer Inc., New York, N.Y.

[21] Appl. No.: 357,229

[22] Filed: Mar. 11, 1982

[30] Foreign Application Priority Data

Mar. 14, 1981 [GB] United Kingdom ............... 8108088

[51] Int. Cl.$^3$ ............... C07D 213/55; A61K 31/44
[52] U.S. Cl. ............... 424/266; 546/321; 546/257; 546/281; 546/283; 546/284; 546/272; 546/167; 546/193; 544/126; 544/360
[58] Field of Search ............... 546/321; 424/266

[56] References Cited

U.S. PATENT DOCUMENTS

| | | | |
|---|---|---|---|
| 3,905,983 | 9/1975 | Bossert et al. | 546/321 |
| 3,943,140 | 3/1976 | Bossert et al. | 546/321 |
| 3,946,027 | 3/1976 | Bossert et al. | 546/257 |
| 3,946,028 | 3/1976 | Bossert et al. | 546/257 |
| 4,177,278 | 12/1979 | Bossert et al. | 424/266 |
| 4,188,395 | 2/1980 | Bossert et al. | 424/266 |

FOREIGN PATENT DOCUMENTS

| | | |
|---|---|---|
| 843576 | 12/1976 | Belgium . |
| 862107 | 6/1978 | Belgium . |
| 865658 | 10/1978 | Belgium . |
| 31801 | 7/1981 | European Pat. Off. . |
| 2248150 | 4/1974 | Fed. Rep. of Germany . |
| 2935772 | 3/1980 | Fed. Rep. of Germany . |
| 55-47656 | 4/1980 | Japan . |
| 1552911 | 9/1979 | United Kingdom . |
| 2034693 | 6/1980 | United Kingdom . |

OTHER PUBLICATIONS

Campbell et al., Chemical Abstracts, vol. 98, No. 5, Abstract No. 34509m, Jan. 31, 1983.

Primary Examiner—Alan L. Rotman
Attorney, Agent, or Firm—Charles J. Knuth; Peter C. Richardson; Allen Bloom

[57] ABSTRACT

Dihydropyridine anti-ischaemic and antihypertensive agents of the formula:

$$R^1OOC \underset{CH_3}{\overset{H \quad R}{\diagup}} COOR^2$$
$$\phantom{R^1OOC}\diagdown_{N}\diagup CH_2{-}O{-}Y{-}NR^3R^4$$
$$\phantom{R^1OOC\diagdown}H$$

(I)

where
Y is —(CH$_2$)$_2$— or —(CH$_2$)$_3$—;
R is aryl or heteroaryl;
R$^1$ and R$^2$ are each independently C$_1$–C$_4$ alkyl or 2-methoxyethyl;
and
R$^3$ and R$^4$ are each independently C$_1$–C$_4$ alkyl or aryl-(C$_1$–C$_4$ alkyl); or R$^3$ and R$^4$ taken together with the nitrogen atom to which they are attached represent a group of the formula:

$$-N\diagdown\diagup, -N\diagdown\diagup O, -N\diagdown\diagup, \text{ or } -N\diagdown\diagup N{-}R^5$$

where R$^5$ is C$_1$–C$_4$ alkyl, aryl, aryl-(C$_1$–C$_4$ alkyl), benzhydryl; 2-methoxyethyl, 2-(N,N-di[C$_1$–C$_4$ alkyl]amino) ethyl, or cyclopropylmethyl;

their pharmaceutically acceptable acid addition salts, processes for the preparation of the compounds, and pharmaceutical compositions containing them.

10 Claims, No Drawings

DIHYDROPYRIDINE ANTI-ISCHAEMIC AND ANTIHYPERTENSIVE AGENTS

BACKGROUND OF THE INVENTION

This invention relates to certain dihydropyridines, specifically to certain 1,4-dihydropyridines having a basic substituted-amino containers group attached to the 2-position, which have utility as anti-ischaemic and antihypertensive agents.

The compounds of the invention delay or prevent the cardiac contracture which is believed to be caused by an accumulation of intracellular calcium under ischaemic conditions (Henry, P. D. et al., Am. J. Physiol. 233, H677, 1977). Calcium overload, during ischaemia, can have a number of additional adverse effects which would further compromise the ischaemic myocardium. These include less efficient use of oxygen for ATP production (Peng, C. F. et al., Circ. Res. 41, 208, 1977), activation of mitochondrial fatty acid oxidation (Otto, D. A. and Ontko, J. A., J. Biol. Chem., 253, 789, 1978), and possibly, promotion of cell necrosis (Wrogemann, K. and Pena, S. D. J. Lancet Mar. 27, p. 672, 1976). Thus the compounds are useful in the treatment or prevention of cardiac conditions, such as angina pectoris, cardiac arrythmias, heart attacks and cardiac hypertrophy. The compounds also possess vasodilator activity and are thus useful as antihypertensives and for the treatment of coronary vasospasm.

SUMMARY OF THE INVENTION

According to the invention, there are provided novel 1,4-dihydropyridine derivatives of the formula:

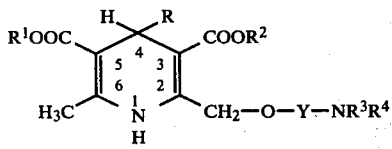

wherein

Y is —(CH$_2$)$_2$— or —(CH$_2$)$_3$—;

R is aryl or heteroaryl;

R$^1$ and R$^2$ are each independently C$_1$–C$_4$ alkyl or 2-methoxyethyl;

and

R$^3$ and R$^4$ are each independently C$_1$–C$_4$ alkyl or aryl-(C$_1$–C$_4$ alkyl); or R$^3$ and R$^4$ taken together with the nitrogen atom to which they are attached represent a group of the formula

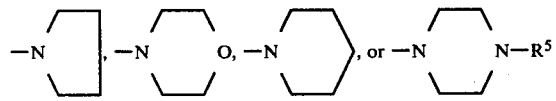

wherein R$^5$ is C$_1$–C$_4$ alkyl, aryl, aryl(C$_1$–C$_4$ alkyl), benzhydryl, 2-methoxyethyl, 2-(N,N-di[C$_1$–C$_4$ alkyl]amino) ethyl or cyclopropylmethyl;

and their pharmaceutically acceptable acid addition salts.

The compounds of the formula (I) containing one or more asymmetric centres will exist as one or more pairs of enantiomers, and such pairs or individual isomers may be separable by physical methods, e.g. by fractional crystallisation of the free bases or suitable salts or chromatography of the free bases. The invention includes the separated pairs as well as mixtures thereof, as racemic mixtures or as separated D- and L-optically-active isomeric forms.

The pharmaceutically acceptable acid addition salts of the compounds of the formula (I) are those formed from acids which form non-toxic acid addition salts containing pharmaceutically acceptable anions, such as the hydrochloride, hydrobromide, hydroiodide, sulphate or bisulphate, phosphate or acid phosphate, acetate, maleate, fumarate, lactate, tartrate, citrate, gluconate and saccharate salts.

The term "aryl" as used in this specification, includes, for example, phenyl optionally substituted by one or two substituents selected from nitro, halo, C$_1$–C$_4$ alkyl, C$_1$–C$_4$ alkoxy, trifluoromethyl, and cyano. It also includes 1- and 2-naphthyl.

The term "heteroaryl" as used in this specification includes, for example, benzofuranyl; benzothienyl; pyridyl optionally mono-substituted by methyl or cyano; quinolyl; benzoxazolyl; benthiazolyl; furyl; pyrimidinyl; and thienyl optionally monosubstituted by halo or C$_1$–C$_4$ alkyl.

"Halo" means fluoro, chloro, bromo or iodo.

C$_3$ and C$_4$ alkyl and alkoxy groups can be straight or branched chain.

The preferred compounds have the formula (I) wherein

R is 1-naphthyl; phenyl optionally monosubstituted by halo, trifluoromethyl, cyano or nitro; thienyl optionally monosubstituted by halo; pyridyl; or quinolyl; and R$^3$ and R$^4$ are each independently C$_1$–C$_4$ alkyl, or benzyl optionally monosubstituted on the aromatic ring portion by halo or C$_1$–C$_4$ alkoxy; or R$^3$ and R$^4$ together with the nitrogen atom to which they are attached represent a group of the formula:

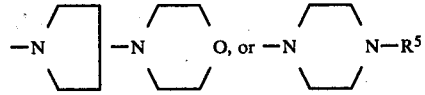

where R$^5$ is C$_1$–C$_4$ alkyl; phenyl optionally monosubstituted by halo; benzyl optionally monosubstituted on the aromatic ring portion by halo; benzhydryl; 2-methoxyethyl; 2-dimethylaminoethyl; or cyclopropylmethyl.

Most preferably, Y is (CH$_2$)$_2$; R is 1-naphthyl or 2-chlorophenyl; R$^1$ and R$^2$ are each independently methyl or ethyl, and R$^3$ and R$^4$ are both methyl.

In a further aspect the invention provides a pharmaceutical composition comprising a compound of the formula (I), or a pharmaceutically acceptable acid addition salt thereof, together with a pharmaceutically acceptable diluent or carrier.

The invention also provides a method of protecting the heart of an animal, including man, from the deleterious effects of ischaemia, which comprises administering to the animal an effective amount of a compound of the formula (I) or pharmaceutically acceptable acid addition salt thereof, or pharmaceutical composition as defined above.

The invention also includes a method of treating hypertension in a human being, which comprises administering to the human being an antihypertensive amount of a compound of the formula (I) or pharmaceutically acceptable acid addition salt thereof, or pharmaceutical composition as defined above.

DETAILED DESCRIPTION OF THE INVENTION

The compounds of the invention may be prepared by a number of routes, including the following:

(1) The compounds may be prepared by the Hantzch synthesis, as follows:

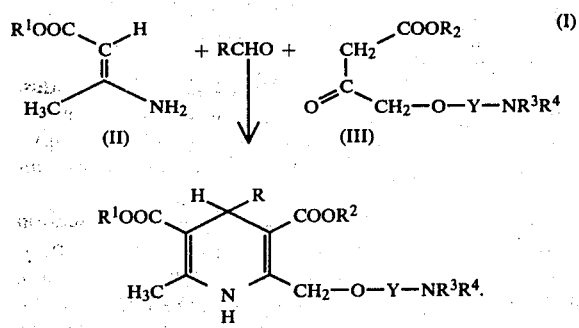

In a typical procedure, the ketoester (III) and aldehyde are heated under reflux in a suitable organic solvent, e.g. a $C_1$-$C_4$ alkanol solvent such as ethanol, for about 15 minutes, and then the crotonate (II) is added. Alternatively the crotonate (II), ketoester (III) and aldehyde can be heated together in the solvent. Preferably a small amount of a lower alkanoic acid such as acetic acid is added to neutralise the solution. The resulting solution can then be heated at 60°-130° C., preferably under reflux, until the reaction is essentially complete, typically in 24 hours or less. The product of the formula (I) can then be isolated and purified by conventional procedures.

The ketoesters (III) are either known compounds or can be prepared by methods analogous to those of the prior art, such as the method illustrated in the Preparation hereinafter, which is essentially the method of Troostwijk and Kellogg, J. C. S. Chem. Comm., 1977, page 932. Similarly the amino-crotonates (II) are either known compounds or can be prepared by conventional procedures. Also the aldehydes are either known or can be prepared by known methods.

(2) The compounds can also be prepared by the following process:

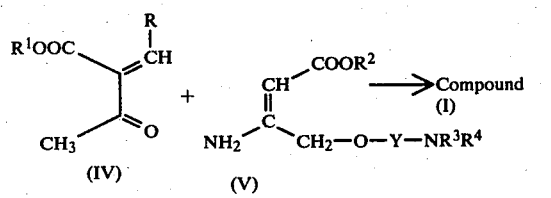

The crotonate (V) is typically prepared in situ by reaction of the corresponding acetoacetate (VI):

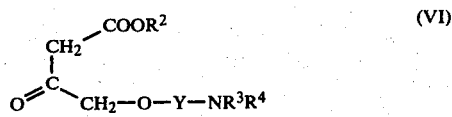

with ammonium acetate, e.g. by refluxing in a suitable organic solvent, e.g. a $C_1$-$C_4$ alkanol such as ethanol, for, say, up to an hour. The crotonate (V) is then reacted with compound (IV), typically by heating in the solvent for up to about 5 hours at 60°-130° C. The product (I) can then be isolated and purified by conventional procedures.

The starting materials (IV) are either known compounds or may be prepared by methods analogous to those of the prior art, see e.g. Can. J. Chem., 1967, 45, 1001.

Pharmaceutically acceptable acid addition salts can be prepared by treating a solution of the free base in a suitable organic solvent with a solution of the appropriate acid in a suitable organic solvent. The acid addition salt may precipitate from solution or can be recovered by conventional procedures.

The compounds of the formula (I) can be administered alone but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions and hypertension, oral dosages of the compounds will be in the range of from 2-50 mg daily for an average adult patient (70 kg). Thus for a typical adult patient, individual tablets or capsules will contain from 1 to 10 mg of active compound, in a suitable pharmaceutically acceptable vehicle or carrier. Dosages for intravenous administration are within the range 1 to 10 mg per single dose as required.

The anti-ischaemic activity of the compounds of the formula (I) is shown by their effectiveness in one or more of the following tests:

(a) delaying the onset of the rise in resting tension (also known as rigor, contracture) in ischaemic isolated guinea-pig hearts; and (b) reducing the ischaemic damage produced in vivo in the guinea-pig heart following intra-ventricular injection of microspherical particles.

In test (a), isolated, electrically driven hearts from male guinea-pigs are perfused in a Langendorff manner with a physiological saline solution (PSS) at 37° C. Test compound, or vehicle, is added to the PSS and after a period of time (typically 20 minutes) the flow of perfusion fluid through the heart is reduced to zero (=ischaemic phase).

During the ischaemic phase, the resting tension of the heart (recorded with a strain-gauge attached to the heart apex) increases, and the test compound at the concentration used is considered to have prevented or delayed the consequences of ischaemia if the increase in resting tension over a period of time (typically 35 minutes) is less than 4 gm.

Compounds are tested at various concentrations in successive heart preparations to determine the approximate minimum effective dose.

In test (b), a suspension of microspherical particles is injected into the left ventricle of the heart of anaesthetised guinea-pigs. A proportion of the particles are carried by the blood into the coronary circulation where they cause a blockage of some small blood vessels. The consequences of this ischaemia may be estimated by changes in the electro-cardiogram over a 30 minute time period OR accumulation of tritium labelled tetracycline into the damaged heart tissue OR release of enzymes from the heart into the blood. In the last two procedures, the animals may be allowed to recover from the anaesthetic and the changes allowed to take place over an extended time period (e.g. 24 hours).

Test compound, or vehicle, is administered to the anaesthetised animal or given prior to anaesthesia.

The antihypertensive activity of the compounds is evaluated after oral administration to spontaneously hypertensive rats or renally hypertensive dogs.

The ability of these compunds to antagonise the effect of $Ca^{++}$ in various tissues is also determined, for example in the rat aorta.

The following Examples illustrate the invention: all temperatures are in °C.:

EXAMPLE 1

Preparation of Diethyl 2-[2-(dimethylamino)ethoxymethyl]-6-methyl-4-(1-naphthyl)-1,4-dihydropyridine-3,5-dicarboxylate and maleate thereof

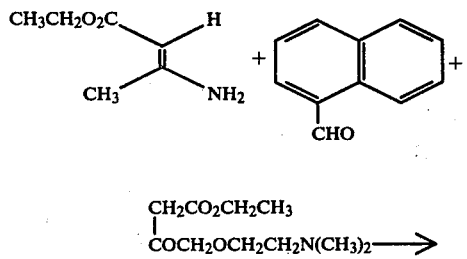

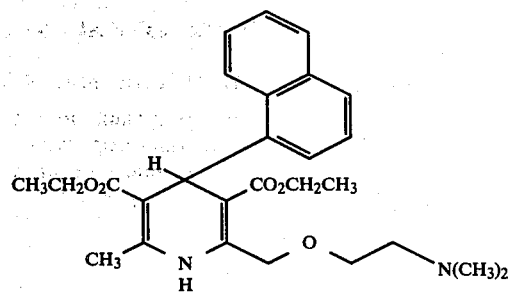

Ethyl 4-[2-(dimethylamino)ethoxy]acetoacetate (4.5 g) and 1-naphthaldehyde (3.1 g) in ethanol (15 ml) were heated under reflux for 15 minutes, then ethyl 3-aminocrotonate (2.6 g) and acetic acid (1 ml) were added and heating was continued overnight (16 hours). The cooled reaction mixture was then evaporated to dryness, and partitioned between toluene (50 ml) and saturated aqueous sodium carbonate (10 ml) to remove acetic acid. The toluene solution was then extracted with 2 N hydrochloric acid and methanol (8:1, 100 ml and 10 ml). The aqueous acid was washed again with toluene (25 ml) then basified with ammonia and extracted with chloroform (2×30 ml). The chloroform extracts were dried ($Na_2CO_3$), filtered and evaporated to dryness. The residue was chromatographed on silica (Merck "Kieselgel" (Trade Mark) 60H, 15 g) in a medium-pressure column, starting in methylene chloride and 60°/80° petrol 2:3, moving gradually to straight methylene chloride. The latter eluted the product which crystallized from ether and was re-crystallized from ether to give the title free base (1.25 g), m.p. 111°–112°.

Analysis %: Calculated for $C_{27}H_{34}N_2O_5$: C,69.50; H,7.42; N,6.01. Found: C,69.33; H,7.39; N,5.86.

The title free base was converted to the *maleate salt* by dissolution in acetone followed by the addition of a slight excess of maleic acid in acetone. Concentration of the solution and addition of ether gave the title maleate salt as colourless crystals, m.p. 159°–160° C.

Analysis %: Calculated for $C_{27}H_{34}N_2O_5 \cdot C_4H_4O_4$: C,63.90; H,6.57; N,4.81. Found: C,63.54; H,6.61; N,4.67.

EXAMPLES 2–30

The following compounds were prepared similarly to the method described in Example 1, and were characterized in the form indicated.

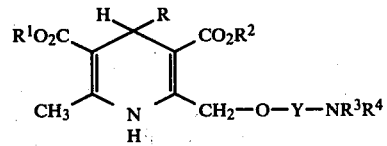

| Example No. | R | $R^1$ | $R^2$ | Y | $-NR^3R^4$ | Form Isolated | m.p. (°C.) | Analysis % (Theoretical in brackets) C | H | N |
|---|---|---|---|---|---|---|---|---|---|---|
| 2 | naphthyl | $-CH_3$ | $CH_2CH_3$ | $-CH_2CH_2-$ | $-N(CH_3)_2$ | free base | 108.5–109.5° | 68.83 (69.00) | 7.20 7.13 | 6.03 6.19 |
| 3 | 2-chlorophenyl | $-CH_3$ | $CH_2CH_3$ | $-CH_2CH_2-$ | $-N(CH_3)_2$ | free base | 106–8° | 60.32 (60.47) | 6.73 6.69 | 6.68 6.41 |
| 4 | naphthyl | $-CH_2CH_3$ | $CH_2CH_3$ | $-CH_2CH_2-$ | 4-(4-chlorobenzyl)piperazin-1-yl | bis-maleate | 160–1° | 61.07 (61.00) | 5.75 6.05 | 4.70 4.85 |
| 5 | 2-chlorophenyl | $-CH_2CH_3$ | $CH_2CH_3$ | $-CH_2CH_2-$ | 4-(4-fluorophenyl)piperazin-1-yl | oxalate | 220° (decomp.) | 58.01 (58.62) | 5.79 5.81 | 6.43 6.21 |
| 6 | 2-(trifluoromethyl)phenyl | $-CH_3$ | $CH_2CH_3$ | $-CH_2CH_2-$ | $-N(CH_3)_2$ | oxalate hydrate | 177° | 51.60 (51.90) | 5.81 5.75 | 4.72 4.84 |
| 7 | 2-chlorophenyl | $-CH_2CH_3$ | $CH_2CH_3$ | $-CH_2CH_2-$ | 4-methylpiperazin-1-yl | bis-oxalate | 202° (decomp.) | 52.49 (52.51) | 5.59 5.88 | 5.76 6.13 |
| 8 | 2-chlorophenyl | $-CH_3$ | $CH_2CH_3$ | $-CH_2CH_2-$ | pyrrolidin-1-yl | free base | 81° | 61.80 (62.26) | 6.87 6.75 | 5.90 6.05 |

-continued

| Example No. | R | R¹ | R² | Y | —NR³R⁴ | Form Isolated | m.p. (°C.) | Analysis % (Theoretical in brackets) C | H | N |
|---|---|---|---|---|---|---|---|---|---|---|
| 9 | 2-Cl-phenyl | —CH₂CH₃ | —CH₂CH₂—O—CH₃ | —CH₂CH₂— | —N(CH₃)₂ | hemihydrate | 88–9° | 58.95 (58.83) | 6.87 (6.99) | 5.76 (5.72) |
| 10 | 1-naphthyl | —CH₃ | —CH₂CH(CH₃)₂ | —CH₂CH₂— | —N(CH₃)₂ | free base | 83–5° | 69.46 (69.97) | 7.79 (7.55) | 5.66 (5.83) |
| 11 | 2-Cl-phenyl | —CH₂CH₃ | —CH₂CH₃ | —CH₂CH₂— | —N(CH₃)₂ | hemihydrate | 108–9° | 59.67 (60.06) | 6.90 (7.01) | 5.99 (6.09) |
| 12 | 1-naphthyl | —CH₃ | —CH₂CH₃ | —CH₂CH₂— | morpholino | free base | 205.5° | 63.44 (63.86) | 6.45 (6.51) | 5.26 (5.32) |
| 13 | 2-Cl-phenyl | —CH₃ | —CH₂CH₃ | —CH₂CH₂— | —N(CH₃)(CH₂-4-F-phenyl) | oxalate | 190–1° | 57.64 (58.02) | 5.68 (5.52) | 4.56 (4.51) |
| 14 | 3-F-phenyl | —CH₃ | —CH₃ | —CH₂CH₂— | —N(CH₃)₂ | oxalate | 116–7° | 55.51 (55.64) | 5.69 (5.89) | 5.36 (5.64) |

-continued

| Example No. | R | R¹ | R² | Y | —NR³R⁴ | Form Isolated | m.p. (°C) | Analysis % (Theoretical in brackets) C | H | N |
|---|---|---|---|---|---|---|---|---|---|---|
| 15 | 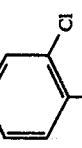 (2-Cl-phenyl) | —CH₂CH₃ | —CH₂CH₃ | —CH₂CH₂— | 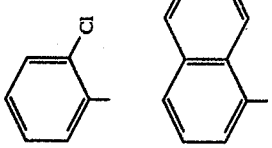 (4-(diphenylmethyl)piperazin-1-yl) | hemi-oxalate | 133–4° | 66.29 (66.61) | 6.75 (6.45) | 5.98 (5.98) |
| 16 | 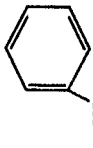 (2-Cl-phenyl) | —CH₃ | —CH₃ | —CH₂CH₂— | —N(CH₃)₂ | hydrate | 97° | 56.78 (57.20) | 6.32 (6.63) | 6.38 (6.35) |
| 17 | 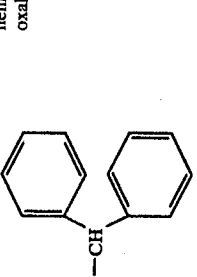 (1-naphthyl) | —CH₂CH₃ | —CH₂CH(CH₃)₂ | —CH₂CH₂— | —N(CH₃)₂ | oxalate | 167–9° | 63.25 (63.68) | 6.82 (6.90) | 4.81 (4.79) |
| 18 | 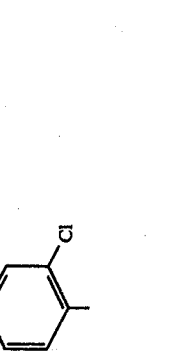 (2-Cl-phenyl) | —CH₃ | —CH₂CH₃ | —CH₂CH₂— | —N(CH₃)(CH₂phenyl) | oxalate | 181° | 59.42 (59.75) | 5.85 (5.85) | 4.39 (4.65) |
| 19 |  (2-thienyl) | —CH₃ | —CH₂CH₃ | —(CH₂)₃— | —N(CH₃)₂ | free base | 66–8° | 59.65 (59.69) | 7.11 (7.16) | 6.51 (6.63) |
| 20 | 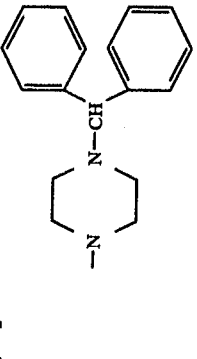 (2-Cl-phenyl) | —CH₃ | —CH₂CH₃ | —CH₂CH₂— | 4-isopropylpiperazin-1-yl | bis-maleate | 172–3° | 55.59 (55.88) | 6.13 (6.16) | 5.54 (5.59) |

-continued

| Example No. | R | R¹ | R² | Y | —NR³R⁴ | Form Isolated | m.p. (°C.) | C | H | N |
|---|---|---|---|---|---|---|---|---|---|---|
| | | | | | | | | \(Theoretical in brackets\) | | |
| 21 | 2-Cl-phenyl | —CH₃ | —CH₂CH₃ | —CH₂CH₂— | N-methylpiperazinyl (N—CH₃) | bis-maleate | 165–7° | 54.51 (54.73) | 5.70 (5.85) | 5.65 (5.80) |
| 22 | 2-Cl-phenyl | —CH₃ | —CH₂CH₃ | —CH₂CH₂— | 4-(4-fluorophenyl)piperazinyl | hydrate | 107° | 61.33 (61.06) | 6.20 (6.32) | 7.05 (7.12) |
| 23 | 2-Cl-phenyl | —CH₃ | —CH₂CH₃ | —CH₂CH₂— | N-(cyclopropylmethyl)piperazinyl | bis-maleate | 157–8 | 56.71 (56.58) | 6.04 (6.07) | 5.53 (5.50) |
| 24 | 2-Cl-phenyl | —CH₃ | —CH₂CH₃ | —CH₂CH₂— | N-(2-methoxyethyl)piperazinyl (OCH₃) | 3.5 maleate | 143–5° | 53.84 (54.20) | 5.97 (6.22) | 5.23 (4.99) |
| 25 | 2-Cl-phenyl | —CH₃ | —CH₂CH₃ | —CH₂CH₂— | N-(2-dimethylaminoethyl)piperazinyl (N(CH₃)₂) | tris-maleate | 167–9° | 53.41 (53.54) | 5.91 (5.95) | 6.14 (6.24) |
| 26 | 3-pyridyl | —CH₃ | —CH₂CH₃ | —CH₂CH₂— | —N(CH₃)₂ | free base | 100–1° | 62.81 (62.51) | 7.36 (7.24) | 10.06 (10.41) |
| 27 | 2-methylthienyl | —CH₃ | —CH₂CH₃ | —CH₂CH₂— | —N(CH₃)₂ | free base | 98° | 58.71 (58.80) | 6.85 (6.91) | 6.70 (6.86) |

-continued

| Example No. | R | R¹ | R² | Y | —NR³R⁴ | Form Isolated | m.p. (°C.) | Analysis % (Theoretical in brackets) C | H | N |
|---|---|---|---|---|---|---|---|---|---|---|
| 28 | 2-bromo-5-methylthiophene | —CH₃ | —CH₂CH₃ | —CH₂CH₂— | —N(CH₃)₂ | free base | 66–7° | 50.59 (50.29) | 5.66 (5.83) | 5.52 (5.59) |
| 29 | 4-methylquinolin-8-yl | —CH₃ | —CH₂CH₃ | —CH₂CH₂— | —N(CH₃)₂ | free base | 128–9° | 66.14 (66.20) | 6.86 (6.89) | 9.04 (9.27) |
| 30 | 3-cyanophenyl | —CH₂CH₃ | —CH₂CH₂— | —N(CH₃)₂ | —N(CH₃)₂ | free base | 105 | 65.11 (64.62) | 6.88 (6.84) | 9.78 (9.83) |

EXAMPLE 31

Preparation of 4-(2-Chlorophenyl)-2-[3-(dimethylamino)propoxymethyl]-3-ethoxycarbonyl-5-methoxycarbonyl-6-methyl-1,4-dihydropyridine:

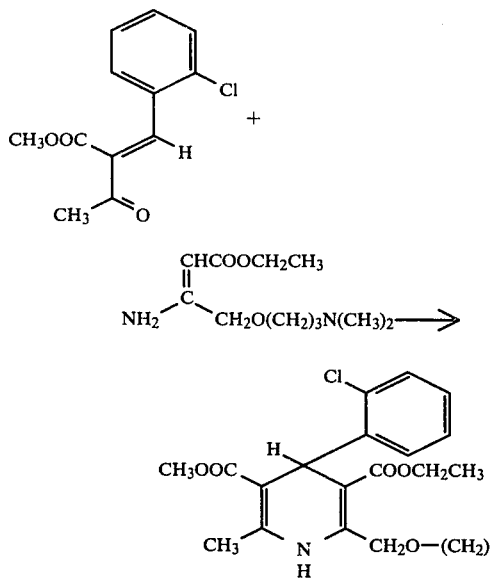

Ethyl 4-[3-(dimethylamino)propoxy]acetoacetate (23 g) was converted to the corresponding 3-aminocrotonate ester by heating in ethanol (50 ml) with ammonium acetate (8 g) for 20 minutes under reflux. Then methyl 2-(2-chlorobenzylidine)acetoacetate (26 g) was added and heating under reflux was continued for 2.5 hours. The reaction mixture was evaporated to dryness and partitioned between toluene (200 ml) and saturated aqueous sodium carbonate (100 ml) to remove acetic acid. The toluene layer was then extracted with 2 N hydrochloric acid (200 ml and 100 ml) and the combined aqueous acid extracts were neutralised (pH 6) with solid sodium carbonate, saturated with sodium chloride, and extracted thoroughly with ethyl acetate (3×200 ml). The combined ethyl acetate extracts were dried (Na$_2$CO$_3$), filtered and evaporated to dryness. The residue in a little toluene was added to a column of silica ("Merck", [Trade Mark] TLC grade, 27 g) made up in 60°/80° petrol containing 20% methylene chloride. Elution was begun with the latter solvent mixture, changing gradually to straight methylene chloride. Appropriate fractions were combined, evaporated to dryness and crystallised from ether and 40°/60° petrol (2:1) to give the title compound as colourless crystals m.p. 77°–8° C. (6.3 g).

Analysis %: Calculated for C$_{23}$H$_{31}$ClN$_2$O$_5$: C,61.26; H,6.93; N,6.21. Found: C,61.01; H,6.90; N,6.30.

EXAMPLES 32–38

The following compounds were prepared similarly to the method described in Example 31:

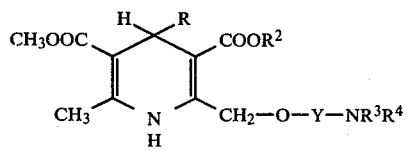

| Example No. | R | R$^2$ | Y | —NR$^3$R$^4$ | Form Isolated | m.p. (°C.) | Analysis % (Theoretical in brackets) C | H | N |
|---|---|---|---|---|---|---|---|---|---|
| 32 | 2-Cl-phenyl | —CH$_2$CH$_3$ | —(CH$_2$)$_3$— | —N(piperazine)N—CH$_3$ | 2.5 maleate | 180° | 54.36 (54.30 | 5.90 5.82 | 5.45 5.28) |
| 33 | 2-Cl-phenyl | —CH(CH$_3$)$_2$ | —(CH$_2$)$_3$— | —N(piperazine)N—CH$_3$ | bis-maleate | 172–4° | 55.27 (55.88 | 6.14 6.16 | 5.33 5.59) |
| 34 | 2-Cl-phenyl | —CH$_2$CH$_3$ | —CH$_2$CH$_2$— | —N(piperazine)N—CH$_2$-(4-Cl-phenyl) | bis-oxalate | 216–7° | 53.75 (53.71 | 5.26 5.28 | 5.20 5.37) |
| 35 | 3-NO$_2$-phenyl | —CH$_2$CH$_3$ | —CH$_2$CH$_2$— | —N(CH$_3$)$_2$ | hydrochloride | 174–5° | 54.02 (54.60 | 6.34 6.25 | 8.72 8.68) |
| 36 | 3-NO$_2$-phenyl | —CH$_2$CH$_3$ | —CH$_2$CH$_2$— | —N(CH$_3$)CH$_2$-(4-OCH$_3$-phenyl) | oxalate | 93–5° | 58.08 (58.03 | 5.81 5.50 | 6.53 6.55) |

| Example No. | R | R² | Y | —NR³R⁴ | Form Isolated | m.p. (°C.) | Analysis % (Theoretical in brackets) C | H | N |
|---|---|---|---|---|---|---|---|---|---|
| 37 | 2-chlorophenyl | —CH₂CH₃— | —CH₂CH₂— | morpholino | free base | 72–4° | 60.39 (60.18 | 6.92 6.52 | 5.54 5.85) |
| 38 | 2-chlorophenyl | —CH₂CH₃ | —CH₂CH₂— | 4-benzyl-1-piperazinyl | bis oxalate | 212–3° | 55.80 (56.19 | 5.62 5.66 | 5.89 5.62) |

The following Preparation illustrates the preparation of a β-ketoester starting material. All temperatures are in °C.

PREPARATION

Ethyl 4-[2-(dimethylamino)ethoxy]acetoacetate

Sodium hydride (50% in oil, 12 g) was stirred in dry tetrahydrofuran (THF) (150 ml) under nitrogen and 2-(dimethylamino)ethanol (21 ml) was added slowly. The resulting warm mixture was stirred for 1 hour, then cooled on an ice bath while a solution of ethyl 4-chloroacetoacetate (20 g) in dry THF (50 ml) was added dropwise over a period of 1 hour. The reaction mixture was stirred at room temperature (20°) overnight, then poured into a mixture of ice-water (100 ml) and concentrated hydrochloric acid (20 ml). Salt was added to saturate the aqueous layer (pH 8) and the mixture was extracted thoroughly with ethyl acetate (4×200 ml). Extracts were dried (MgSO₄), filtered and evaporated to an oil. This was dissolved in acetonitrile (100 ml) was washed with petrol (60°/80°, 50 ml) to remove mineral oil. Evaporation of the acetonitrile gave ethyl 4-2-(dimethylamino)ethoxy acetoacetate as an oil (16.5 g, 62%) characterized by its n.m.r. spectrum, δ(CDCl₃) p.p.m.: 1.26 (3H,t); 2.26 (6H,s); 2.52 (2H,t); 3.59 (2H,t); ca 3.6 (2H, broad); 4.11 (2H,s); 4.16 (2H,q).

The following ketoesters were prepared similarly to the above, and were characterized by n.m.r.:
Ethyl 4-[2-(1-pyrrolidinyl)ethoxy]acetoacetate;
Ethyl 4-[2-(4-{4-chlorobenzyl}-1-piperazinyl)ethoxy]acetoacetate;
Ethyl 4-[2-(4-benzyl-1-piperazinyl)ethoxy]acetoacetate;
Ethyl 4-[2-(4-methyl-1-piperazinyl)ethoxy]acetoacetate
Ethyl 4-[3-(dimethylamino)propoxy]acetoacetate;
Ethyl 4-[2-(4-{4-fluorophenyl}-1-piperazinyl)ethoxy]acetoacetate;
2-Methoxyethyl 4-[2-(dimethylamino)ethoxy]acetoacetate;
Iso-Butyl 4-[2-(dimethylamino)ethoxy]acetoacetate;
Ethyl 4-[2-(morpholino)ethoxy]acetoacetate;
Ethyl 4-[2-(N-{4-fluorobenzyl}methylamino)ethoxy]acetoacetate;
Ethyl 4-[2-(N-{4-methoxybenzyl}methylamino)ethoxy]acetoacetate;
Ethyl 4-[2-(4-benzyhydryl-1-piperazinyl)ethoxy]acetoacetate;
Ethyl 4-[2-(N-benzylmethylamino)ethoxy]acetoacetate;
Ethyl 4-[2-(4-cyclopropylmethyl-1-piperazinyl)ethoxy]acetoacetate;
Ethyl 4-[2-(4-{2-methoxyethyl}-1-piperazinyl)ethoxy]acetoacetate;
Ethyl 4-[2-(4-{2-dimethylaminoethyl}-1-piperazinyl)ethoxy]acetoacetate;
Ethyl 4-[3-(4-methyl-1-piperazinyl)propoxy]acetoacetate;
Methyl 4-[2-(dimethylamino)ethoxy]acetoacetate; and
Ethyl 4-[2-(4-isopropyl-1-piperazinyl)ethoxy]acetoacetate.

These ketoesters tend to polymerise on storage at room temperature but can be kept for a few weeks at 0° C.

We claim:
1. A compound of the formula

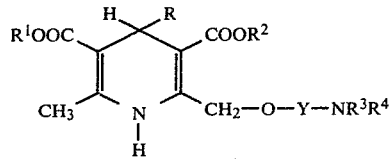

or a pharmaceutically acceptable acid addition salt thereof,
wherein
Y is —(CH₂)₂— or —(CH₂)₃—;
R is aryl;
R¹ and R² are each independently C₁–C₄ alkyl or 2-methoxyethyl;
and
R³ and R⁴ are each independently C₁–C₄ alkyl or aryl-(C₁–C₄ alkyl);
wherein said aryl is phenyl; phenyl substituted by one or two substituents selected from nitro, halo, C₁–C₄ alkyl, C₁–C₄ alkoxy, trifluoromethyl, and cyano; or is 1- or 2-naphthyl.

2. A compound of claim 1 wherein
R is 1-naphthyl; phenyl; or phenyl monosubstituted by halo, trifluoromethyl, cyano or nitro; and
R³ and R⁴ are each independently C₁–C₄ alkyl, or benzyl optionally monosubstituted on the aromatic ring portion by halo or C₁–C₄ alkoxy.

3. A compound of claim 2 wherein Y is (CH₂)₂; R is 1-naphthyl or 2-chlorophenyl; R¹ and R² are each independently methyl or ethyl; and R³ and R⁴ are both methyl.

4. A compound of claim 3 wherein R is 2-chlorophenyl, R¹ is methyl and R² is ethyl.

5. A compound of claim 3 wherein R is 1-naphthyl and $R^1$ and $R^2$ are each ethyl.

6. A pharmaceutical composition comprising an anti-ischaemic or antihypertensive effective amount of a compound of claim 1 and a pharmaceutically acceptable diluent or carrier.

7. A pharmaceutical composition of claim 6 wherein Y is $(CH_2)_2$; R is 1-naphthyl or 2-chlorophenyl; $R^1$ and $R^2$ are each independently methyl or ethyl; and $R^3$ and $R^4$ are both methyl.

8. A method of treating hypertension in an animal in need of treatment comprising administering to said animal an effective anti-hypertensive amount of a compound of claim 1.

9. A method of treating ischaemia in an animal in need of treatment comprising administering to said animal an effective anti-ischaemic amount of a compound of claim 1.

10. A method according to claim 8 or claim 9 wherein Y is $(CH_2)_2$; R is 1-naphthyl or 2-chlorophenyl; $R^1$ and $R^2$ are each independently methyl or ethyl; and $R^3$ and $R^4$ are both methyl.

* * * * *